United States Patent [19]

Bryant et al.

[11] Patent Number: 5,053,022

[45] Date of Patent: Oct. 1, 1991

[54] APPLICATOR FOR INTRANASAL ADMINISTRATION OF VACCINES TO HORSES

[75] Inventors: Sharon A. Bryant, Shawnee, Kans.; Karen K. Brown, Kansas City, Mo.; Richard E. Parizek, Lenexa, Kans.; Larry F. Moore, Greenwood; Louis J. Travalent, Lee's Summit, both of Mo.

[73] Assignee: Mobay Corporation, Pittsburgh, Pa.

[21] Appl. No.: 546,210

[22] Filed: Jun. 28, 1990

[51] Int. Cl.[5] .......... A61M 31/00

[52] U.S. Cl. .......... 604/278; 604/275; 604/49; 119/51.01

[58] Field of Search .......... 604/278, 275, 257, 264, 604/239, 48, 49, 104; 119/51.01

[56] References Cited

U.S. PATENT DOCUMENTS

| | | | |
|---|---|---|---|
| 4,410,320 | 10/1983 | Dystra et al. | 604/48 |
| 4,432,758 | 2/1984 | Finegold | 604/278 |
| 4,500,513 | 2/1985 | Brown et al. | 424/89 |

OTHER PUBLICATIONS

Galan et al, "Mucosal Nasopharyngeal Immune Responses of Horses to Protein Antigens . . . ", *Infection and Immunity*, Mar. 1985, pp. 623–628.

Polly et al, "Protective Studies with a Group A Streptococcal . . .", *The Journal of Infectious Diseases*, vol. 131, Mar. 1975, pp. 217–224.

D'Alessandri, et al, "Protective Studies with Group A Streptococceal . . . ", *The Journal of Infectious Diseases*, vol. 138, No. 6, 1978.

*Primary Examiner*—John D. Yasko

*Attorney, Agent, or Firm*—Joseph C. Gil; Lyndanne M. Whalen

[57] ABSTRACT

A device for administering antigenic material to a horse intranasally. This device is composed of a hollow tube and a blocking device. The hollow tube is long enough to reach the tonsilor tissue of a horse. This tube has a sealed end and a tapered open end. At least one opening, preferably openings along the length of this tube are positioned in a manner such that antigenic material which exits through them will reach the tonsilor tissue of the horse. The blocking device sits on the hollow tube at the point where the tapering of the open end begins. A syringe containing antigenic material is positioned at the tapered open end of the hollow tube and the antigenic material is then released in the form of small droplets on the tonsilor tissue of the horse.

8 Claims, 1 Drawing Sheet

APPLICATOR FOR INTRANASAL ADMINISTRATION OF VACCINES TO HORSES

BACKGROUND OF THE INVENTION

The present invention relates to a device for the administration of liquids such as vaccines to a horse intranasally and to a method of administering liquids such as vaccines to a horse intranasally using this device.

Several traditional techniques for administering vaccines and other medical preparations to horses are known. One of those known techniques is intranasal vaccination. U.S. Pat. No. 4,500,513, for example, discloses intranasal application of flu vaccine to horses. Galan et al, "Mucosal Nasopharyngeal Immune Responses of Horses to Protein Antigens of *Streptococcus equi*", *Infection and Immunity,* March 1985, pages 623–628; Polly et al, "Protective Studies with a Group A Streptococcal M Protein Vaccine. Challenge of Volunteers after Local Immunization in the Upper Respiratory Tract", *THE JOURNAL OF INFECTIOUS DISEASES,* Vol. 131, No.3, March 1975, pages 217–224; and D'Alessandri, et al, "Protective Studies with Group A Streptococcal M Protein Vaccine. III. Challenge of Volunteers after Systemic or Intranasal Immunization with Type 3 or Type 12 Group A *Streptococcus*", THE JOURNAL OF INFECTIOUS DISEASES, Vol.138, No.6, December 1978, pages 712–718 each discuss intranasal challenges of horses.

The delivery of an intranasal vaccination to a horse presents special problems, however, because of the structure of the horse's nose. A vaccine should be delivered to the tonsilor tissue which is typically about 12 to about 20 inches (i.e., about 30 to about 50 cm) back from the nasal orifice. The normal technique for nasal application is by atomized spray as is discussed in the above mentioned D'Alessandri et al and Polly et al articles. However, delivery of an adequate dose into a horse's nose would require approximately five minutes and horses have virtually no tolerance for the hissing noise associated with such atomizers. Challenges such as those discussed in the above-mentioned Galan et al article are therefore normally conducted by sedating the horse prior to exposure to the atomized spray.

It would therefore be advantageous to develop a device to deliver a vaccine or other liquid antigenic material intranasally in a manner which did not require the use of the annoying atomizers or require sedation prior to administration of the vaccine.

Devices suitable for intranasal administration of antigenic materials to horses other than those discussed in the above-mentioned articles are not available commercially. Devices suitable for use by humans are not suitable for use in horses because of the significant difference between the nose structures of horses and of humans.

SUMMARY OF THE INVENTION

It is an object of the present invention to provide a device suitable for delivering a liquid material such as a vaccine to a horse intranasally which device does not make it necessary to sedate the horse prior to administration of the liquid.

It is also an object of the present invention to provide a method for administering a liquid preparation such as a vaccine to a horse intranasally in which such a device is employed.

It is a further object of the present invention to provide a device and method for administering a vaccine to a horse intranasally without significantly disturbing the horse.

These and other objects which will be apparent to those skilled in the art are accomplished by means of a flexible tube made of a polymeric material such as polypropylene which is long enough to reach the tonsilor tissue of a horse. This flexible tube is open at one end which end is tapered to allow insertion of a syringe. The opposite end of this tube is sealed. This flexible tube has one or more openings positioned on the side of the tube at a distance such that when the tube is inserted into the nostril of the horse dissemination of a liquid preparation such as a vaccine as a fine mist will occur. A disc or similar object having an opening adapted to fit over the applicator tube but not over the flanged section of the tube is positioned just above the point where the tube becomes flanged. This disc prevents accidental injection of the applicator up the horse's nose during the inoculation process. The vaccine or other liquid preparation to be administered is injected by a syringe attached to the flanged section of the applicator through the tube. The injected material exits the applicator tube through the opening(s) located on the side(s) of the tube and is thus applied as a mist to the tonsilor tissue of the horse.

DETAILED DESCRIPTION OF THE INVENTION

Figure 1:
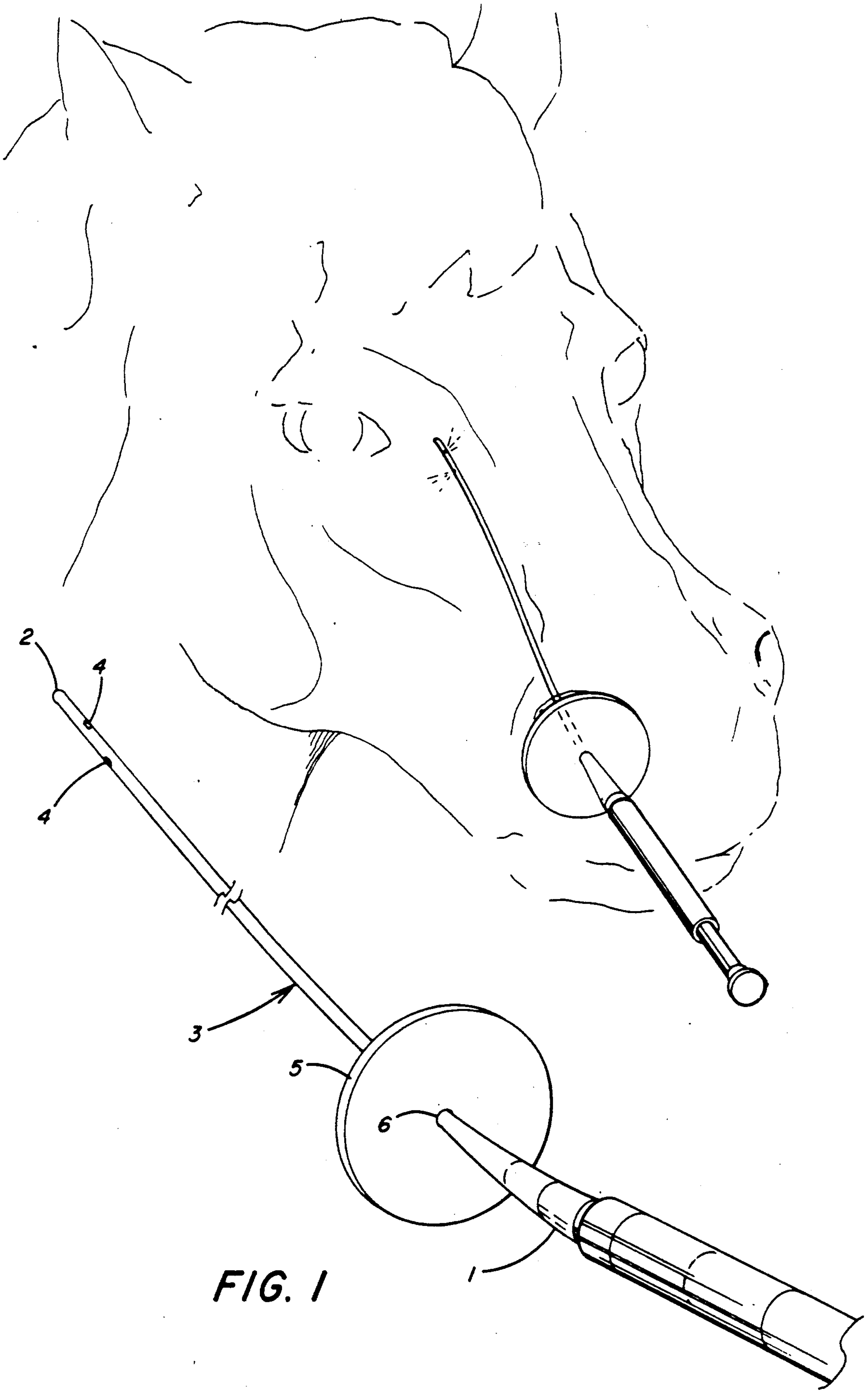
FIG. 1 illustrates an intranasal applicator within the scope of the claimed invention.

The intranasal applicator of the present invention is a hollow tube 3 which is open at one end 1 and sealed at the other end 2. This tube 3 is made of a flexible material, preferably a flexible polymeric material which is bendable so that it will not injure the tissue inside the nasal passage but stiff enough to make it possible to insert the applicator into the nose of the horse without curling up. Examples of suitable materials are polypropylene and high density polyethylene. Polypropylene is particularly preferred. This tube 3 is long enough to reach the tonsilor tissue of the horse, generally about 5 to about 15 inches (12.7–38.1 cm) long, preferably about 8 to about 12 inches (20.3–30.5 cm) long and most preferably about 8 to about 10 inches (20.3–25.4 cm) long. The tube 3 may have any diameter which fits within the nasal cavity of the horse and allows a liquid injected by syringe at the open end to reach the tonsilor tissue of the horse. It is preferred that the tube 3 (excluding the diameter of the tapered open end 1) have an outer diameter of from about 0.045 in. (1.1 mm) to about 0.060 in. (1.5 mm), most preferably from about 0.045 inch (1.1 mm) to about 0.050 in. (1.3 mm) and an inner diameter of at least about 0.02 in. (0.5 mm), preferably from about 0.02 in. (0.5 mm) to about 0.03 in. (0.76 mm). The wall thickness of the flexible tube is preferably from about 0.005 in. (0.13 mm) to about 0.015 in. (0.38 mm).

The open end 1 of the tube 3 is adapted to receive a syringe. It is preferred that the tube be tapered or flanged so that the syringe will fit tightly into the opening.

The tube 3 also has at least one hole or opening 4 located along its length at positions such that liquid material exiting these holes or openings 4 will reach the tonsilor tissue of the horse in the form of a mist. If more than one opening is present, it is advantageous to have the openings 4 positioned at points around the circumference of the tube such that the liquid material exiting those holes will reach all sides of the nasal cavity of the horse. This is generally accomplished by having from about 2 to about 4 holes or openings, preferably 2 holes or openings positioned on opposite sides of the circumference of the tube. In a preferred embodiment of the invention, one opening is located approximately 0.25 inch (6.35 mm) from the sealed end of the tube 2 and a second opening is located approximately 0.5 inch (12.7 mm) from the sealed end of the tube 2. The diameters of these holes or openings 4 need only be large enough to permit liquid exiting through the openings to exit in the form of small droplets or a spray. Appropriate diameters for these holes 4 are generally from about 0.028 inch (0.7 mm) to about 0.035 inch (0.89 mm) preferably 0.030 inch (0.76 mm).

Another component of the applicator of the present invention is a blocking object or device 5 which is adapted to fit over the tapered open end of the applicator tube and to prevent the applicator plus syringe from entering the nasal cavity of the horse during intranasal administration of a vaccine. This blocking device 5 may be any device capable of achieving both of these requirements. The blocking device 5 illustrated in FIG. 1 is a round disc having an opening 6 through which the applicator tube 3 will pass until the tapered end 1 which has been adapted to receive a syringe is reached. This disc blocking device 5 is preferred because of its simplicity but a disc of any other shape could also be used. The opening 6 through which the applicator tube passes need not be positioned in the center of this blocking device 5 but it has been found that it is much easier to use devices in which the opening is approximately in the center. The opening 6 of the blocking device 5 should have a diameter which is sufficiently greater than the outer diameter of the applicator tube 3 to permit the blocking device 5 to slide over the applicator tube 3 but not great enough that the tapered open end of the applicator tube 1 will pass through the opening 6. This blocking device 5 may be made of any material, including the same material used to make the applicator tube 3 but it is preferred that it be made of a relatively stiff polymeric material which does not readily bend so that it can not pass into the nasal cavity of the horse. Suitable materials include: polypropylene, high density polyethylene and styrene.

The device of the present invention is particularly useful for intranasal application of vaccines and other antigenic materials to horses. More specifically, a syringe containing the antigenic material to be administered is prepared in accordance with generally accepted practice. This syringe is then slid into the tapered end 1 of applicator tube 3 until it is snugly positioned in the opening. The blocking device 5 is then positioned over the applicator tube 3. The applicator tube 3 is then positioned in the nasal cavity of the horse and the antigenic material is injected through the applicator tube 3. The antigenic material then exits the holes in the form of small droplets which fall upon the tonsilor tissue of the horse.

Appropriate doses of specific antigenic materials to be administered using the device of the present invention are known to those skilled in the art.

Having thus described our invention, the following Example is given as being illustrative thereof.

EXAMPLE

The applicator illustrated in FIG. 1 made of polypropylene having a wall thickness of approximately 0.009 inch (0.23 mm), an inner diameter of approximately 0.27 inch (0.7 mm) and an outer diameter of 0.045 inch (1.1 mm), a first opening located approximately 0.25 inch (6.35 mm) from the sealed end and a second opening located approximately 0.5 inch (12.7 mm) from the sealed end was used to administer *Streptococcus equi* vaccine to 10 horses in accordance with the teachings of U.S. Ser. No. 90,272. No difficulty in administering the vaccine intranasally was experienced even though the horses were not sedated prior to administration of the vaccine.

Although the invention has been described in detail in the foregoing for the purpose of illustration, it is to be understood that such detail is solely for that purpose and that variations can be made without departing from the spirit and scope of the invention except as it may be limited by the claims.

What is claimed is:

1. A device for administering antigenic material to a horse intranasally which device is composed of
   a. a hollow flexible tube which (1) is long enough to reach the tonsilor tissue of a horse, (2) is sealed at one end and has an open tapered end adapted to receive a syringe and (3) has at least one opening positioned along its length through which the antigenic material may exit in the form of small droplets so that the exiting antigenic material will fall upon the tonsilor tissue of the horse and
   b. a blocking device containing an opening sufficiently large that the flexible tube will pass therethrough until the blocking device reaches the tapered open end of the tube.
2. The device of claim 1 in which the hollow flexible tube is made of polypropylene and is from about 8 to about 10 inches long.
3. The device of claim 1 in which the hollow flexible tube has an inner diameter of 0.02 inch, excluding the tapered end, adapted to receive a syringe.
4. The device of claim 1 in which the blocking device is a round disc having a hole located in its center.
5. The device of claim 1 in which the hollow tube has an outer diameter of from about 0.045 inch to about 0.050 inch.
6. The device of claim 1 in which the flexible tube is from about 8 to about 10 inches long.
7. The device of claim 1 in which the flexible tube has a wall thickness of from about 0.005 to about 0.015 inches.
8. A method for administering an antigenic material to a horse intranasally in which the antigenic material is placed in a syringe, the syringe is positioned in a device composed of (a) a hollow flexible tube which (1) is long enough to reach the tonsilor tissue of a horse, (2) is sealed at one end and has an open tapered end adapted to receive a syringe and (3) has at least one opening positioned along its length through which the antigenic material may exit in the form of small droplets so that the exiting antigenic material will fall upon the tonsilor tissue of the horse and (b) a blocking device containing an opening sufficiently large that the flexible tube will pass therethrough until the blocking device reaches the tapered open end of the tube at the tapered open end and the antigenic material is then released from the syringe.

* * * * *